US012279075B2

(12) United States Patent
Burger et al.

(10) Patent No.: US 12,279,075 B2
(45) Date of Patent: Apr. 15, 2025

(54) MEDICAL IMAGING SYSTEM AND METHOD OF CONTROLLING SUCH IMAGING SYSTEM

(71) Applicant: BHS Technologies GmbH, Innsbruck (AT)

(72) Inventors: Gregor Burger, Völs (AT); Mark Capelli, Innsbruck (AT); Michael Santek, Götzens (AT)

(73) Assignee: BHS Technologies GmbH, Innsbruck (AT)

( * ) Notice: Subject to any disclaimer, the term of this patent is extended or adjusted under 35 U.S.C. 154(b) by 0 days.

(21) Appl. No.: 17/574,638

(22) Filed: Jan. 13, 2022

(65) Prior Publication Data

US 2022/0224864 A1 Jul. 14, 2022

(30) Foreign Application Priority Data

Jan. 13, 2021 (EP) .................................... 21151440

(51) Int. Cl.
| | |
|---|---|
| *H04N 7/18* | (2006.01) |
| *A61B 90/00* | (2016.01) |
| *A61B 90/50* | (2016.01) |
| *H04N 23/50* | (2023.01) |
| *H04N 23/66* | (2023.01) |

(52) U.S. Cl.
CPC ............. *H04N 7/183* (2013.01); *A61B 90/37* (2016.02); *H04N 23/66* (2023.01); *A61B 2090/373* (2016.02); *A61B 2090/502* (2016.02); *H04N 23/555* (2023.01)

(58) Field of Classification Search
CPC ............... H04N 7/183; H04N 5/23203; H04N 2005/2255; A61B 90/37; A61B 2090/373; A61B 2090/502; A61B 2090/368; A61B 2090/372; A61B 34/20; A61B 90/20; A61B 90/361; G06F 3/011; G06F 3/012; G06F 9/451; G16H 30/40; G16H 40/63; G02B 27/0172
USPC .......................................................... 348/65
See application file for complete search history.

(56) References Cited

U.S. PATENT DOCUMENTS

| | | | |
|---|---|---|---|
| 9,898,662 B2* | 2/2018 | Tsuda ..................... | A61B 34/25 |
| 2016/0069743 A1* | 3/2016 | McQuilkin ............ | A22B 5/007 |
| | | | 356/416 |
| 2016/0148052 A1* | 5/2016 | Tsuda ..................... | G06V 20/20 |
| | | | 345/633 |
| 2017/0151034 A1* | 6/2017 | Oda ....................... | A61B 90/37 |
| 2021/0165556 A1* | 6/2021 | Panse ..................... | G06F 3/011 |

FOREIGN PATENT DOCUMENTS

| | | |
|---|---|---|
| JP | 2018-022316 | 2/2018 |
| WO | WO 2015/008469 | 1/2015 |
| WO | WO 2018/210645 | 11/2018 |

* cited by examiner

*Primary Examiner* — Christopher S Kelley
*Assistant Examiner* — Asmamaw G Tarko

(57) ABSTRACT

The present invention relates to a medical imaging system (1, 1') comprising a control device (2, 2'), an imaging device (3) and at least two head-mounted display systems (4a, 4b, 4c, 4d), wherein the control device (2, 2') is configured to assign different sets of control functions to the at least two head-mounted display systems (4a, 4b, 4c, 4d), respectively.

11 Claims, 2 Drawing Sheets

MEDICAL IMAGING SYSTEM AND METHOD OF CONTROLLING SUCH IMAGING SYSTEM

RELATED APPLICATION

This application claims the benefit of priority of Europe Patent Application No. 21151440.1 filed on Jan. 13, 2021, the contents of which are incorporated herein by reference in their entirety.

FIELD AND BACKGROUND OF THE INVENTION

The present invention relates to a medical imaging system and a method of controlling such imaging system.

For different procedure, like microsurgical procedures in plastic surgery or neurosurgery, more than one operator, like surgeons or assistants, need to receive images from an imaging device. To provide such images, several monitors as digital imaging devices may be arranged in an operating room to be visibly accessible from different operators in different positions. However, the displayed images on such monitors are not individually adapted to operative requirements of an operator or assistant. In particular, the displayed images may provide an inversed orientation with respect to the position or viewing orientation of the operator. The respective viewing angle may also cause a poor visibility of the image, specifically preventing or decreasing a three-dimensional impression of three-dimensional images. Further, the space in an operating room for arranging several monitors is limited.

In addition or alternatively to the arrangement of several monitors analogous devices may be used. For example, a medical microscope may provide a second ocular system as a so-called "spy" to allow a second operator to receive images. Since such second ocular system is mounted to the medical imaging device and therefore in a fixed relative position to the first ocular system for a main operator or the like, such relative position may not comply with desired ergonomics, e.g. with respect to different heights of operators or their respective positions. Furthermore, the light of the imaging device may have to be distributed on two ocular systems. For example, 70% of light are assigned to the first ocular system and 30% of light are assigned to the second ocular system. As a result, the maximum amount of light with respect to 100% is not available for any of the ocular systems and the second ocular may not be capable of providing the same quality of images in comparison to the first ocular depending on the respective light distribution.

Accordingly, it is an object of the present invention to provide an improved medical imaging system and a method of controlling such medical imaging system capable of displaying images to more than one operator in sufficient quality.

SUMMARY OF THE INVENTION

The object is solved by a medical imaging system, and a method of controlling such medical imaging system according to the present invention. Further aspects of the present invention are subject of the dependent claims.

According to one aspect, the medical imaging system comprises a control device, an imaging device and at least two head-mounted display systems, wherein the control device is configured to assign different sets of control functions to the at least two head-mounted display systems, respectively.

In principle, a head-mounted display provides more flexibility for an operator to move within a particular space and to change an orientation while still being able to view images displayed by the head-mounted display system. Further, any sharing or distribution of images by being displayed by more than one head-mounted display system is not subject to a reduced imaging quality due to the digital character, i.e. data transfer only. However, different operators may have the respective images according to individual needs, for example, with respect to operative requirements and/or personal preferences. Furthermore, different operators may have restricted rights to access different control functions. Accordingly, the control device is configured to assign different sets of control functions to the at least two head-mounted display systems to comply with such individual settings. The control device may be implemented as separate control device or implemented in at least one of the head-mounted displays and/or the medical imaging device. If each head-mounted display provides a control device, the head-mounted display system may configured to select one of the control devices as master control device for the assignment of control functions to avoid conflicting authorizations. Such selection may be based, for example, on a registration order, a personal authorization identification or the like. The selection may be adapted, e.g. to allow to transfer the control of an assignment from one operator to another.

For example, a first head-mounted display system may be assumed as master head-mounted display system to be used by a main operator like a surgeon. A second head-mounted display system may be assumed as an assistant head-mounted system to be used by an assistant like a secondary surgeon, a surgical assistant, an anesthesiologist, a scrub nurse or the like. Accordingly, the control device may be configured to assign a first set of control functions to the first head-mounted display system and a second set of control functions different from the first set of control functions to the second head-mounted display system, respectively. The first set of control functions and the second set of control functions differ in at least one functionality. Such functionality may be directed to a particular function as such and/or to an extent to execute a respective function. An assignment of a set of control functions may also comprise an assignment of no control function, i.e. the set of control functions is set to zero. In such event, the respective head-mounted display may only receive a respective medical image. Such medical image may than be displayed as recorded or adapted according to the control functions of the other head-mounted display to which the different set of control functions has been assigned to. With respect to an adaption of the head-mounted display system by control functions of the other head-mounted display, the control device may be configured to cause such adaption in parallel or only on demand by the other head-mounted display in accordance with a respective control function. The control device may also be configured to cause such adaption in parallel for specific control functions and only on demand by the other head-mounted display for other specific control functions. Such adaption may not necessarily apply for all control functions.

In some embodiments, a first set of control functions to be assigned comprises at least one control function of the imaging device.

Control functions of the imaging device may include but are not limited to displacement functions to move the imaging device from one position to another, posture functions to change an orientation or viewing angle of the imaging device, and/or imaging functions like the magnification by the imaging device, color settings, contrast settings and/or brightness. Accordingly, at least one of the control functions provided by the imaging device may be controlled by the first set of control functions. The control device may be configured to allow the execution of such control function or functions by the first set of control commands only, or also by the imaging device in parallel. A respective assignment of control functions of the imaging device to be executed by the first set of control functions and/or by the imaging device as such or another respective control of the imaging device may differ depending on a specific control function. For example, any control function that may affect a surgeon's direct view on a situs during surgery may only be assigned to the first set of control functions intended to be assigned to the head-mounted display system of the surgeon. However, imaging functions like color or contrast settings may not provide a severe risk and may be assigned to the imaging device or another respective control in parallel.

Advantageously, control functions of the imaging device should be assigned to a set of control functions intended to be assigned to a head-mounted display to be used by an operator responsible and mainly affected by respective control functions. For example, any control function that may constitute a risk for a patient during surgery by affecting the work of a surgeon may be assigned exclusively to the surgeon. As another example, when responsibilities with respect to different control functions are assigned to different operators, it may be favorable to assign each control function only once to avoid conflicting control commands by different operators.

Preferably, a second set of control functions to be assigned is configured to exclude control functions of the imaging device.

Accordingly, a second head-mounted display system with the second set of control functions may be prevented from interfering control functions of the imaging device controlled by a first head-mounted display system and/or other control devices. Thus, the security is enhanced. The exclusion of control functions of the imaging device may be directed to the exclusion of all control functions of the imaging device or to some selected control functions of the imaging device, in particular, control functions of the imaging device prone to causing conflicts and/or security risks.

However, the control device may be configured to assign respective control functions of the imaging device to the second set of control functions and, therefore, to the second head-mounted display system on demand, e.g. by a respective control function of the first set of control functions and/or another input device for such release. For example, two surgeons may be responsible for different tasks during a surgery. One surgeon may be associated with the first head-mounted display with the first set of control functions assigned thereto comprising control functions of the imaging device. The other surgeon may be associated with the second head-mounted display system with the second set of control functions excluding control functions of the imaging device in a first setting. When the one surgeon has finished a particular task, the one surgeon may assign or release a specific control function or set of control functions of the imaging device to the second set of control functions of the second head-mounted display to support another respective task by the other surgeon.

Even though control functions of the medical imaging device may be excluded from the second set of control functions, an operator provided with the second set of control functions may still be able to alter an image by control functions that allow different settings of the displayed image by the head-mounted display system.

In some embodiments, the imaging system comprises different access points to connect the head-mounted display systems to the control device, and the control device is configured to assign the different sets of control functions based on a respective access point the head-mounted display system is connected to or an order of connecting the head-mounted display system to an access point.

An access point may be provided by a wired interface or configured as wireless access point. With respect to a wired interface, a first set of control functions may be assigned to a first head-mounted display system connected to a wired interface associated with the first set of control functions. Accordingly, a second set of control functions may be assigned to a second head-mounted display system connected to a wired interface associated with the second set of control functions. Similarly, wireless access points to which a head-mounted display system is connected to or associated with may represent different sets of control functions. The control device may be configured to assign at least one set of control functions only once. For example, the control device may be configured to assign a set of control functions associated with one access point only to the head-mounted display system connected or detected first.

Alternatively or in addition, a head-mounted display system may be configured to provide an identification signal associated with a specific set of control functions. With respect to the option of providing an identification signal in addition to the assignment of a set of control functions by a respective access point, a further access restriction with respect to an available set of control functions may be provided. For example, an assignment of a set of control functions may not only require the access of an access point by a head-mounted display system but also a corresponding identification signal confirming a required authorization.

In some embodiments, the control device may also be configured to provide different set of control functions to a plurality of head-mounted display systems, e.g. depending on an access order and/or identification signal or other kind of authorization. For example, a first set of control functions comprising control functions of the imaging device may be assigned to a head-mounted display accessing the access point first and/or providing an identification signal indicating the authorization to receive such control functions first. A second set of control functions, e.g. excluding all or at least some of the control functions of the imaging device, may be assigned to one or more second head-mounted display systems subsequently accessing the access point and/or providing an identification signal with a lower level of control rights.

In some embodiments, the control device is configured to assign the different sets of control functions based on a predefined personal identification of an operator associated with a head-mounted display system.

A personal identification of an operator may be provided by personal badge or an input device to receive a personal password and/or fingerprint. The respective personal identification is associated with at least one specific set of control functions. However, if specific set of control functions is intended to be only assigned once or only to another restricted number of operators, the assignment of such set of control functions may also be combined with a control of already conducted assignments of such set of control functions. The control device may also be configured to assign different roles to operators by the personal identification and/or by the identification signal of a head-mounted display system to allow different operators to overrule an assignment. As an example, if a first set of control functions is intended to be assigned only once and the first set of control functions is assigned to an assistant, a surgeon providing a respective personal identification or equipped with a head-mounted display system providing a respective identification signal may be able to request such first set of control functions. The control device may be configured to transfer the first set of control functions directly upon such request or after a further confirmation by the surgeon and/or assistant. A further confirmation may avoid any disturbance of a sensitive task by a sudden change of available control functions. After such transfer, the assistant may be automatically provided with a another set of control functions not in conflict with the first set of control functions or may have reapply for another set of control functions, e.g. via another access point or the like. Similarly, a priority of assignments and respective changes may be implemented by prioritizing specific access points.

Preferably, the imaging system comprises a user interface, and the control device is configured to assign the different sets of control functions based on an operator's input with respect to the user interface.

As alternative or in addition to the above, the user interface may allow a respective assignment or change of an assignment with respect to an operator's input. An operator's input may require a further identification of access rights to the user interface in advance, e.g. by entering a password or by providing another personal identification as per a badge or fingerprint. Alternatively or in addition, the operator associated with respective access rights may be identified by a tracking system. The further identification may also provide different access level. For example, lower authorization levels associated with a particular identification may be limited to assign only low level sets of control functions, e.g. set of control function not in conflict with the control of the imaging device, while higher authorization levels associated with another particular identification may be authorized to assign also higher level sets of control functions that may include control functions of the imaging device up and may be further authorized to change already assigned set of control functions. The user interface may be provided as graphical user interface but may also be simply provided as a footswitch.

In some embodiments, the user interface may be displayed in at least one of the head-mounted display to be controlled by an operator, for example, by tracking an eye and/or head movement as operator's input. Accordingly, the assignment of control functions or a respective change of an assignment may be executed via the head-mounted display.

In some embodiments, the imaging system comprises a tracking system configured to track a position and/or spatial orientation of at least one of the head-mounted display systems to adapt the image displayed by a head-mounted display of the head-mounted display system in accordance with the tracked position and/or spatial orientation, and/or a user interface to adapt the image displayed by a head-mounted display of the head-mounted display system in accordance with an user input.

Accordingly, the respective head-mounted display system may be capable of displaying an image by the imaging system in an orientation corresponding to the position and/or spatial orientation of the operator provided with such head-mounted display system. Therefore, the respective operator may move from one side of an operating table to another side with the displayed image being mirrored accordingly. Such adaption may be implemented to be executed constantly or on demand. Further, the adaption may be provided automatically by each set of control functions or may only be provided by specific sets of control functions.

Preferably, the tracking system comprises an identification of the respective access point the head-mounted display system is connected to, as described above, representative of the position and/or spatial orientation.

Each access point may be associated with an approximated position and/or spatial orientation of a head-mounted display system registered by such access point. Even though a viewing angle may differ from such position and/or spatial orientation, the approximation may provide a sufficient match with respect to usual orientations in view of relevant tasks. Due to only approximating a position and/or spatial orientation, the tracking system may be less complex while still providing sufficient basis for an adaption of images displayed.

Preferably, the tracking system comprises a sensor-based detection of the position and/or spatial orientation.

Due to a sensor-based detection of the position and/or spatial orientation may be more accurate. In particular, the more accurate detection may be required for sensitive surgeries to avoid any adaption of the image displayed deviating from a real orientation of the head-mounted display representing an operator's orientation.

Further, a combination of tracking positions and/or spatial orientations by access points and sensors may be used as plausibility check of tracked positions and/or spatial orientations.

Advantageously, the control device is configured to assign the different sets of control functions and/or adapt the control functions based on the tracked position and/or spatial orientation.

For example, a set of control functions including control functions of the imaging device may only be assigned to head-mounted display system within a predetermined distance to the medical imaging device or a situs, respectively. Consequently, the imaging device is prevented to be controlled by a person not in sufficient visible contact to the imaging device or the like. Accordingly, the control device may be configured to disable specific control functions of an assigned set of control functions in dependence of the tracked position and/or spatial orientation for the same reasons. An adaption of control functions may also comprise an enabling of additional control functions.

The assignment of different sets of control functions and/or adapt the control functions based on the tracked position and/or spatial orientation may also be directed to a change of assignments and/or adaptions from one head-mounted display system to another. For example, a first set of control functions may always be assigned to a head-mounted display system tracked as being nearest to the imaging device or situs, respectively. However, the control device may further provide security mechanisms like confirmation requests and/or fulfillment of predetermined authority requirements to avoid any unintended change.

In some embodiments, the control device is configured to release at least one control function of at least one set of control functions in accordance with a separate activation action.

As some of the control functions may be sensitive of being executed unintentionally with severe consequences, a separate activation requirement enhance the safety of the use of the imaging system. Such activation may be required in advance and/or constantly during execution of a control function. An example of a device for such activation action may be a footswitch. Alternatively or in addition, an activation action may comprise a voice signal, gesture or the like.

Advantageously, the imaging device is a medical microscope, in particular, a robotic medical microscope, or an endoscope.

The imaging system as described above allow a sterile control of an imaging device and/or respective images displayed. In particular, more than one operator may be capable of receiving images in sufficient quality and adaptable to personal needs depending with respect to their responsibilities and tasks to be conducted. The assignment of different set of control functions may ensure a safe control of the imaging device. All of the advantages are particularly relevant for medical microscopes, specifically robotic medical microscopes, or endoscopes. When it comes to minimally invasive surgeries, images of the point of interest are only accessibly via a reproduction of images of the imaging devices. Therefore, it is important to provide such images with the advantages as described above.

In another aspect, the present invention is directed to a method of controlling an imaging system according to the above disclosure, comprising the steps of:
identifying at least one of the at least two head-mounted display systems, and
assigning a set of control functions to the at least one identified head-mounted display system based on the identification.

As described above, the identification may relate to a personal identification by an operator, an identification signal by the head-mounted display system, a specific access point and/or a tracking system. The respective assignment of a concrete set of control functions may be based on the identification in terms of an identification characteristic representative of an order of identification, e.g. whether the head-mounted display is identified first or second and so on, a particular access point, an authorization level and/or user interface input.

In some embodiments, the identification step comprises the identification of at least two head-mounted display systems, and different set of control functions are assigned to the respective head-mounted display systems.

In particular, the one set of control functions may comprise control functions of the imaging device while the other set of control functions does not comprise at least those functions or any control functions of the imaging device at all. Consequently, any interferences with respect to the control of the imaging device may be avoided.

Advantageously, the imaging system comprises more than two head-mounted display systems and at least one set of control functions is assigned only once to one of the head-mounted display systems.

Similarly as per the above, when more than two head-mounted display systems are identified, the set of control functions comprising control functions of the imaging device is preferably assigned only once to one head-mounted display system. Another set of control functions may be assigned to the other head-mounted display systems. However, the sets of control functions assigned to the other head-mounted displays may also differ. In other words, one head-mounted display system may be assumed with as master head-mounted display system associated with a respectively assigned master set of control functions, while the other head-mounted display system or systems may be assumed as assistant head-mounted display system or systems associated with a respectively assigned assistant set of control functions. The assistant set of control functions may be representative of assistant sets of the same or different control functions.

BRIEF DESCRIPTION OF THE SEVERAL VIEWS OF THE DRAWINGS

Further advantages, aspects and details of the disclosure are subject to the claims, the following description of preferred embodiments applying the principles of the disclosure and drawings. In particular:

DESCRIPTION OF SPECIFIC EMBODIMENTS OF THE INVENTION

Figure 1:
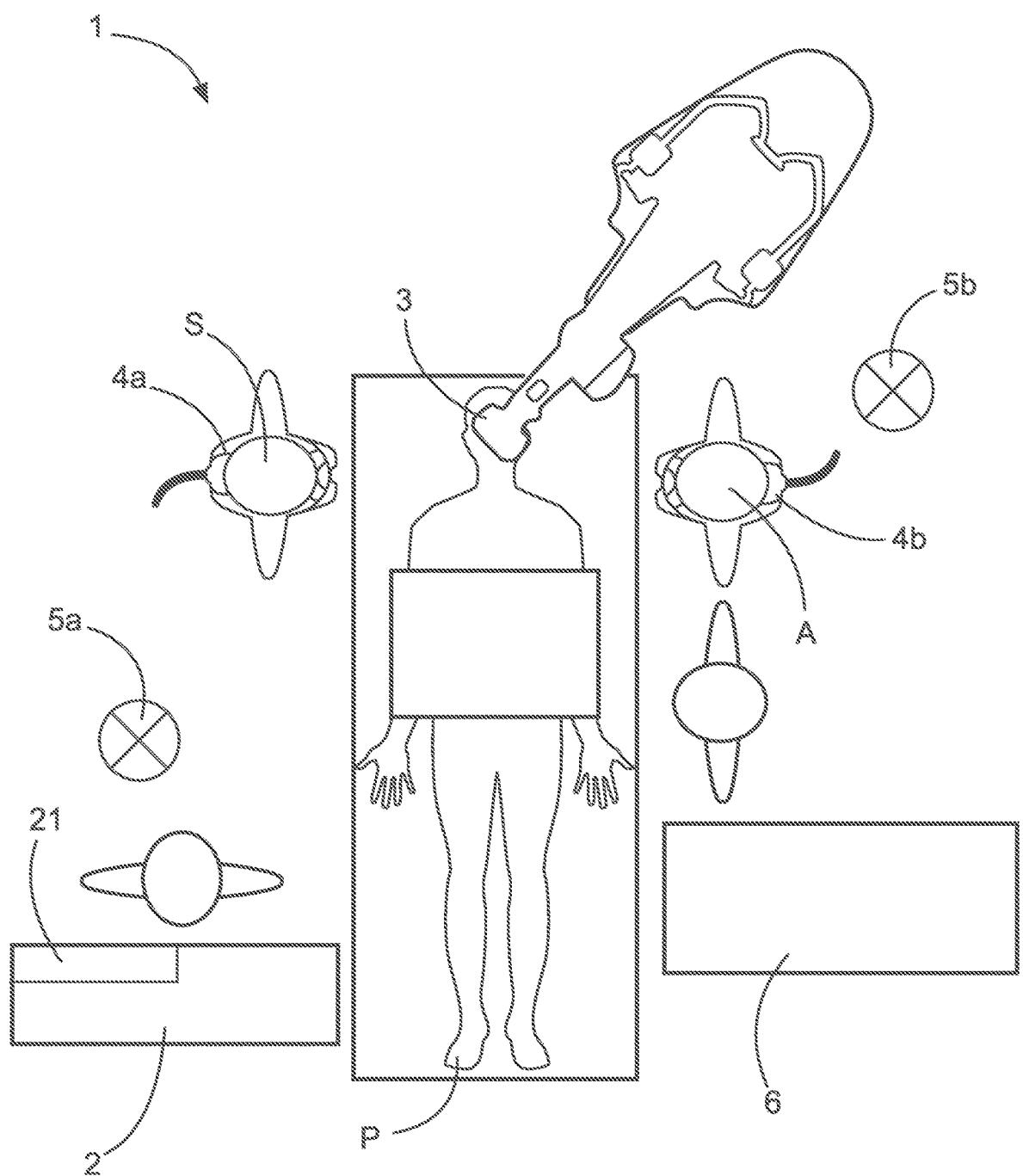
FIG. 1 is a schematic top view on a medical imaging system within a surgical environment according to a first exemplary embodiment of the present invention.

FIG. 1 shows a schematic top view on a medical imaging system 1 within a surgical environment according to a first exemplary embodiment of the present invention. The exemplary medical imaging system 1 comprises a control device 2, an imaging device 3 and two head-mounted display systems 4a, 4b. According to the first embodiment, the imaging device 3 is a robotic medical microscope to provide images of a patient P. Each of the head-mounted display systems 4a, 4b is configured to allow images of the imaging device 3 to be displayed by at least on display of the head-mounted display systems 4a, 4b to a respective operator wearing such head-mounted display system 4a, 4b. The head-mounted display system 4a is associated with a surgeon S and the head-mounted display system 4b is associated with an assistant A, as illustrated in FIG. 1. Since the surgeon S and the assistant A may be responsible for different tasks during a medical procedure or the like and may also be located in different positions with respective different orientations, personal preferences and requirements with respect to display settings and functions may differ. Further, the head-mounted display systems 4a, 4b are capable of providing further control functions to control the imaging device 3 and/or other peripheral devices. However, some control functions may be sensitive and may interfere with a current task of another operator. As an example, the assistant A may interfere a procedure executed by the surgeon S, who relies on the images provided by the medical imaging device 3, when the assistant A affects such images by controlling the imaging device 3, which could result in serious effects on the patient P. To avoid any conflicting interference or to at least reduce such risk, the control device 2 is configured to assign different sets of control functions to the head-mounted display systems 4a, 4b. Even though a first set of control functions assigned to the head-mounted display system 4a associated with the surgeon S and a second set of control functions assigned to the head-mounted display system 4b associated with the assistant A may provide the same control functions with respect to display settings and display functions the first and second set of control functions differ in the ability to control the imaging device 3. According to the present embodiment, control functions to control the imaging device 3 are only provided by the first set of control functions assigned to the head-mounted display system 4a or to the surgeon S, respectively. Accordingly, the assignment of different sets of control functions is configured as a master-slave-system to provide a first set of control functions with control functions and a second set of control functions with only a limited number of the defined control functions released. In the present embodiment, the first set of control functions associated as master set of control functions comprises at least one control functions to allow a control of at least one control function of the second set of control functions associated as slave set of control functions. For example, if the surgeon S associated with the first set of control functions intends provide the assistant A with a particular view on a detail of an image, the surgeon S may be authorized to adapt the image displayed by the head-mounted display system 4b associated with the assistant A accordingly, e.g. by zooming in. However, the first and second set of control functions may also be configured to provide individual configurations according to personal preferences and/or requirements as a variant of the first embodiment. Further, the control device 2 is configured to adapt the first and second set of control commands and/or the assignment thereof. Such adaption is implemented, for example, by a respective input using a user interface 21 or other assignment or adaption criteria as described later.

The assignment of the first and second set of control functions dependents on the identification of the respective head-mounted display system 4a, 4b and/or the respective operator S, A. Here, an ID is assigned to head-mounted display system 4a associated with a surgeon S. Such ID is transmitted to the control device 2 wireless connection. However, the ID may also be transmitted by a wire connection in addition or alternatively as a variant of the first embodiment. Upon receipt of the ID, the control device 2 assigns a first set of control functions to the head-mounted display system 4a. Such assignment is executed by releasing control functions implemented in the respective head-mounted display system 4a, 4b. Alternatively or in addition, the assignment may be executed by providing such control functions to the respective head-mounted display system 4a, 4b and/or by the control device 2 being a recipient of control functions of the respective head-mounted display systems 4a, 4b configured to only forward control functions to be executed if assigned to a respective set of control functions. The transfer of an ID to the control device is not restricted to a direct transfer to the control device but may also comprises an indirect transfer, as via access points 5a, 5b like in the present embodiment.

The access points 5a, 5b are configured to connect with the head-mounted display systems 4a, 4b. Such connection is implemented wirelessly, e.g. by Bluetooth, Bluetooth Low Energy and/or WLAN. Alternatively or in addition, the connection between the access points 5a, 5b may be implemented by a wired interface in a variant of the first embodiment. The access points 5a, 5b are configured to receive an ID of the head-mounted display systems 4a, 4b and/or the operators S, A. In a variant, the access points may be configured to assign a respective ID to the head-mounted display systems 4a, 4b. Further, the access points 5a, 5b are configured to assign a set of control functions to the head-mounted display systems 4a, 4b. Accordingly, the access points are also connected wirelessly to the control device 2 for the assignment of the different sets of control functions. Alternatively, the connection may be implemented as wired connection. In accordance with the above, the assignment of the different sets of control functions is executed indirectly via the respective access points 5a, 5b by the control device 2. In a variant, the assignment may be executed directly to the head-mounted display systems 4a, 4b. The access points 5a, 5b may also be configured to process received identification data associated with the head-mounted display systems 4a, 4b and/or the respective operator S, A to reduce the amount of data to be processed by the control device 2.

The assignment of a set of control functions based on an operator's ID is also implemented via the user interface 21 identifying an operator S, A and registering a head-mounted display system 4a, 4b associated with the identified operator S, A. The identification may be based on an individual pin or a pin representing a predetermined authority level. Similarly, an ID of an operator may be transmitted to the control device for identification of an operator and registering purposes by a badge, a fingerprint and/or other identification procedures and corresponding receiving means. In the present embodiment, the control device 2 is configured to assign the first or second set of control functions depending on the ID received by the access points 5a, 5b. Further, the control device is configured to adapt such assignment based on an authorized input via the user interface 21. Such adaption may comprise an adaption of the control functions associated with a first and/or second set of control functions and/or an adaption of the assignment of the first and/or second set of control functions. In a variant, a registration of the head-mounted display systems 4a, 4b and/or the operator S, A may be required as prerequisite for an assignment of the first and/or second set of control functions via connection to one of the access points 5a, 5b.

The assignment of a set of control functions depending on an operator's ID may increase a security level as the assignment of a set of control function may be linked to a certain level of education, experience, specific skills and the like. However, an assignment in dependence of a head-mounted display system 4a, 4b may provide advantages, for example, if different operators with a same level of authority with respect to the assignment of a set of control functions request the reception of a set of control functions. The assignment depending on an operator's ID and depending on an ID of a head-mounted display system 4a, 4b may be combined. As an example, two operators with the same level of authority as first assignment criterion are identified by the control device 2. Accordingly, the assignment of the different set of control functions is based on the ID of the respective head-mounted display systems 4a, 4b as second assignment criterion.

Alternatively or in addition, further assignment criteria may be applied by the control device 2, e.g. an order of identification, a spatial position associated with the identification or a type of procedure to be executed. The control device 2 is also configured to adapt assignment criteria based on predetermined settings, procedures or events.

In the present embodiment, as described previously, the assignment of a first or second set of control functions is based on the ID of the head-mounted display system 4a, 4b associated with the first set of control functions or second set of control functions, respectively, as first assignment criterion. As second assignment criterion or as adaption criterion, a user input via the user interface 21 is implemented. However, a spatial position as assignment criterion may be implemented in a variant. With respect to a spatial position, the access points 5a, 5b may be associated with such position. For example, access point 5a may be associated with the usual position of the surgeon S and access point 5b with the usual position of the assistant A. Accordingly, when the head-mounted display system 4a is connected to access point 5a, the control device 2 assigns the first set of control functions associated with the surgeon S to the head-mounted display system 4a. The connection may be established by a wired connection or by the head-mounted display system 4a entering a predetermined detection area of the access point 5a with respect to a wireless connection. The predetermined detection area may be defined by the detection ability of the access point 5a by individual setting that may be adapted according to different boundary conditions and requirements. Analogously, when the head-mounted display system 4b is connected to access point 5b, the control device 2 assigns the second set of control functions associated with the assistant A to the head-mounted display system 4b. The determination of a spatial position in accordance with the connection to a respective access point 5a, 5b may be combined with further criteria like an identification of the head-mounted display systems 4a, 4b and/or an identification of the respective operator S, A to determine whether such identification qualifies for the respective assignment. Further, the control device 2 may be configured to withdraw a respective assignment when the respective head-mounted display system 4a, 4b is disconnected from the respective access point 5a, 5b. Such disconnection may be due to a disconnection of a wired connection between the head-mounted display system 4a, 4b from the respective access point 5a, 5b or due to the head-mounted display system 4a, 4b being moved outside the predetermined detection area of the connected access point 5a, 5b. For example, the control device 2 may withdraw an assignment of the first set of control functions to the head-mounted display system 4a associated with the surgeon, the head-mounted display system 4a is no longer detected by the access point 5a or the detected position is outside the predetermined detection area indicating, for example, that the surgeon S has left the operating room. Accordingly, the head-mounted display system 4a may be blocked from executing the first set of control functions previously assigned. Alternatively, the control device 2 may be configured to adapt the first set of control functions or to assign a different set of control functions to the head-mounted display system in the event of a disconnection from the access point 5a or in dependence of a predetermined detection area, for example, to exclude control functions sensitive to risk associated with a spatial position. The same may apply for the head-mounted display system 4b associated with the assistant A with respect to a previous assignment of the second set of control functions.

The medical imaging system 1 further comprises a tracking system 6 configured to track a position and/or spatial orientation of at least one of the head-mounted display systems 4a, 4b to adapt the image displayed by a head-mounted display of the head-mounted display system 4a, 4b in accordance with the tracked position and/or spatial orientation. Alternatively or in addition, the image displayed by a head-mounted display of the head-mounted display system 4a, 4b may be adapted via the user interface 21 in accordance with a user input. The adaption of the displayed image comprises, for example, the change of the image orientation to display the image in an orientation corresponding to the orientation of the head-mounted display system 4a, 4b. For example, the imaging device 3 is set as reference orientation. When the orientation of head-mounted display system 4a associated with the surgeon A is detected to deviate from the reference orientation, the orientation of the displayed image is adapted accordingly. The same applies for the head-mounted display system 4b associated with the assistant A. However, as such may not be required in any event or even undesired under certain circumstances, the first and second set of control functions comprise the control function to activate and deactivate the adaption of the orientation of the displayed image.

The tracking system 6 is configured to directly track the position and/or spatial orientation of the respective head-mounted display system 4a, 4b. Alternatively or in addition, the tracking system may be configured to indirectly track such position by tracking the position and/or spatial orientation of the operator S, A associated with the respective head-mounted display system 4a, 4b. In particular, if the tracking position is configured to track a position and/or spatial orientation of the operator S, A associated with the respective head-mounted display system 4a, 4b a security level may be enhanced since the a respective adaption is directly linked to the operator S, A. A further enhancement of the security level may be achieved by tracking the position and/or spatial orientation of the head-mounted display system 4a, 4b and the associated operator S, A. In such event, a predetermined difference between a position and/or spatial orientation of the head-mounted display system 4a, 4b and a position and/or spatial orientation of the respectively associated operator S, A may indicate that the respective head-mounted display system 4a, 4b is not worn at all or not worn in an appropriate manner by the respective operator S, A. Accordingly, the control device 2 may be configured to initiate an alert and/or to block at least some sensitive control functions of the assigned set of control functions.

In a further variant, the tracking system 6 may be configured to replace the access points 5a, 5b. In such event, the assignment of the first and second set of control functions may be based on a position criterion only and/or on the detection order of the head-mounted display systems 4a, 4b and or respective operators S, A associated with the head-mounted display systems 4a, 4b. Further adaptions of the respective assignment may be implemented via the user interface 21.

According to another variant, the access points 5a, 5b may be configured to comprise tracking functions. Accordingly, the access points 5a, 5b may not only be configured to receive an ID of the head-mounted display system 4a, 4b connected thereto and to monitor whether the respective head mounted-display system 4a, 4b is within a predetermined detection area but is also capable of providing a concrete spatial position and/or orientation of the head-mounted display system 4a, 4b and/or the operator S, A.

Figure 2:
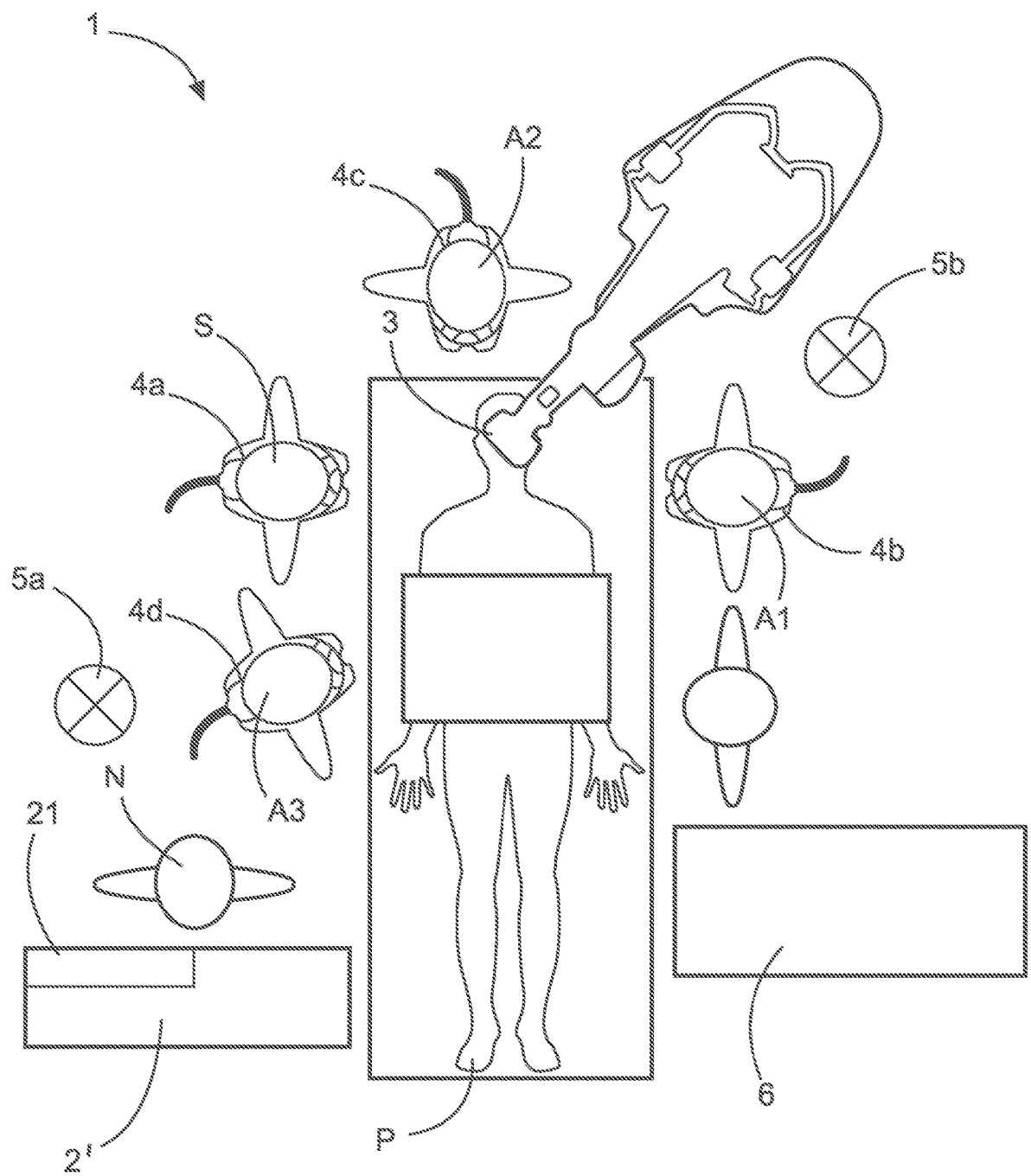
FIG. 2 is a schematic top view on a medical imaging system within a surgical environment according to a second exemplary embodiment of the present invention.

FIG. 2 shows a schematic top view on a medical imaging system 1' within a surgical environment according to a second exemplary embodiment of the present invention.

While the first embodiment relates to the assignment of a first and second set of control functions to head-mounted display systems 4a, 4b, the second embodiment relates to the assignment of set of control functions to more than two head-mounted display systems 4a, 4b, 4c, 4d. In principle, the second embodiment may be assumed as an enhancement of the first embodiment with respect to dealing with more than two head-mounted display systems 4a, 4b, 4c, 4d. Accordingly, the components and respective functionalities of the second embodiment do not differ from the first embodiment. However, the control device 2' of the second embodiment is configured to process more than two assignments of sets of control functions. In such context, it is noted that the control device 2 of the first embodiment may also be configured to process more than two assignments. However, for explanation reasons only, the assignment of sets of control functions to more than two head-mounted display systems 4a, 4b, 4c, 4d is described with respect to the second embodiment.

According to the second embodiment, the control device 2' of the medical imaging device 1' is configured to assign different set of control functions to four head-mounted display systems 4a, 4b, 4c, 4d. However, the assignment may not be restricted to the four head-mounted display systems 4a, 4b, 4c, 4d and the control device 2' may also be configured to provide three assignments or more than four. Here, the control device 2' is configured to assign to each head-mounted display system 4a, 4b, 4c, 4d a different set of control functions. Specifically, the control device 2' is configured to assign a first set of control functions to be assigned to the head-mounted display system 4a associated with a surgeon S, a second set of control functions to the head-mounted display system 4b associated with an assistant A1, a third set of control functions to the head-mounted display system 4c associated with an assistant A2 and a fourth set of control functions to the head-mounted display system 4d associated with an assistant A3. In a variant, the control device 2' may be configured to not necessarily assign different sets of control functions to each of the head-mounted display systems 4a, 4b, 4c, 4d but at least two different sets of control functions. For example, the control device 2' assigns the first set of control functions to the head-mounted display system 4a associated with the surgeon S and the second set of control functions to the head-mounted display systems 4b, 4c, 4d associated with the assistants A1, A2, A3. Accordingly, the assignment by the control device 2' may depend on a role of an operator S, A associated with the respective head-mounted display system 4a, 4b, 4c, 4d. The roles associated with a respective head-mounted display 4a, 4b, 4c, 4d may not be limited to surgeons and assistants. For example, a third set of control functions may be assigned to a head-mounted display system associated with a scrub nurse.

Analogously to the first embodiment, the head-mounted display systems 4a, 4b, 4c, 4d are connected wirelessly to the access points 5a, 5b by entering a respective detection area. Here, the head-mounted display system 4a associated with the surgeon S and the head-mounted display system 4d associated with the assistant A3 are connected to access point 5a and transfer their respective IDs to the control device 2' via access point 5a. The same applies for the head-mounted display system 4b associated with the assistant A1 and the head-mounted display system 4c associated with the assistant A2 with respect to access point 5b.

The respective assignment in dependence of a received ID by the control device or the control functions of a respective set of control functions may be altered via the user interface 21. A respective input may be provided by the surgeon S or any other authorized person. Here, for reasons of sterility, a nurse N is authorized to request respective adaptions via the user interface 21. Alternatively or in addition, other assignment and adaption criteria may be considered by the control device 2' as already described with respect to the first embodiment, for example, an order of the head-mounted displays connected to the access points 5a, 5b, an operator's ID alternatively or in addition to an ID of the head-mounted display system 4a, 4b, 4c, 4d associated with such the head-mounted display system 4a, 4b, 4c, 4d, a spatial position of the head-mounted display system 4a, 4b, 4c, 4d and/or respective operator S, A1, A2, A3 and the like.

It is to be noted that the given examples are specific embodiments and not intended to restrict the scope of protection given in the claims. In particular, single features of one embodiment may be combined with another embodiment.

LIST OF REFERENCE SIGNS 1, 1' medical imaging system
2, 2' control device
3 imaging device
4a, 4b, 4c, 4d head-mounted display system
5a, 5b access point
6 tracking system
21 user interface
A, A1, A2, A3 assistant (operator)
N nurse
P patient
S surgeon (operator)

What is claimed is:

1. A medical imaging system comprising:
   an imaging device adapted to perform a plurality of imaging device functions;
   at least two head-mounted display systems—(HMDs) for displaying medical images captured by the medical imaging device;
   a control device configured to assign a first set of functions from the plurality of imaging device functions to one of the at least two HMDs and a second set of functions from the plurality of imaging device functions to another of the at least two HMDs;
   wherein a difference between the first set and the second set involves at least one of:
      a displacement function for moving the imaging device,
      a posture function for changing at least one of an orientation and a viewing angle of the imaging device, and
      an imaging function for capturing medical images;
   wherein the control device configured to assign the first and second sets based on at least one of:
   an access point through which at least one of the at least two HMDs connects to the control device,
   an order in which the at least two HMDs connect to the access point, and
   at least one of a tracked position and a spatial orientation of at least one of the at least two HMDs.

2. The medical imaging system according to claim 1, wherein a difference between the sets involves a control function to exclude control functions of the imaging device.

3. The medical imaging system according to claim 1, wherein the control device is configured to assign the first and second sets based on a predefined personal identification of an operator (S, A) associated with a one of the at least two head-mounted display systems.

4. The medical imaging system according to claim 1, further comprising a user interface, and wherein the control device is configured to assign the first and second sets based on an operator's (S, A) input with respect to the user interface.

5. The medical imaging system according to claim 1, further comprising a tracking system that comprises an identification of the respective access point, wherein the medical imaging system comprises a plurality of different access points to connect the at least two HMDs to the control device.

6. The medical imaging system according to claim 5, wherein the tracking system comprises at least one of a sensor-based detection of the position and a spatial orientation.

7. The medical imaging system according to claim 1, wherein the control device is configured to release at least one control function from the first set of control functions in accordance with a separate activation action.

8. The medical imaging system according to claim 1, wherein the imaging device is at least one member of a group consisting of: a medical microscope, a robotic medical microscope, and an endoscope.

9. A method of controlling a medical imaging system according to claim 1, comprising the steps of:
- identifying at least one of the at least two head-mounted display systems, and
- assigning a set of control functions to the at least one identified head-mounted display system based on the identification.

10. The method according to claim 9, wherein the identification step comprises the identification of at least two head-mounted display systems, and wherein different set of control functions are assigned to the respective head-mounted display systems.

11. The method according to claim 9, wherein the medical imaging system comprises more than two head-mounted display systems and at least one set of control functions is assigned only once to one of the head-mounted display systems.

\* \* \* \* \*